United States Patent
Zimmer et al.

(10) Patent No.: US 7,597,900 B2
(45) Date of Patent: Oct. 6, 2009

(54) TISSUE ABRASIVES

(75) Inventors: Jose Zimmer, Ingelheim (DE); Sean Lee, Karlsruhe (DE); Coni Rosati, Encinitas, CA (US)

(73) Assignee: Schott AG, Mainz (DE)

( * ) Notice: Subject to any disclaimer, the term of this patent is extended or adjusted under 35 U.S.C. 154(b) by 709 days.

(21) Appl. No.: 10/696,878

(22) Filed: Oct. 30, 2003

(65) Prior Publication Data

US 2004/0151745 A1    Aug. 5, 2004

Related U.S. Application Data

(63) Continuation-in-part of application No. 10/673,596, filed on Sep. 29, 2003, now abandoned, which is a continuation-in-part of application No. 09/818,466, filed on Mar. 27, 2001, now Pat. No. 7,250,174.

(51) Int. Cl.
    *A61K 8/02*    (2006.01)
(52) U.S. Cl. .................. 424/401; 424/404; 424/443; 424/446; 424/447; 424/448
(58) Field of Classification Search .......... 424/401, 424/404, 443, 447, 448, 446
See application file for complete search history.

(56) References Cited

U.S. PATENT DOCUMENTS

| | | | |
|---|---|---|---|
| 4,814,165 A | | 3/1989 | Berg et al. |
| 5,290,544 A | | 3/1994 | Shimono et al. |
| 5,766,611 A | | 6/1998 | Shimono et al. |
| 6,224,888 B1 | | 5/2001 | Vatter et al. |
| 6,423,343 B1 * | | 7/2002 | Lee et al. ............ 424/489 |
| 6,517,863 B1 * | | 2/2003 | LaTorre et al. ............ 424/447 |
| 6,589,928 B1 * | | 7/2003 | Lee .................... 510/382 |
| 6,663,878 B1 * | | 12/2003 | Greenspan et al. ........ 424/422 |
| 6,756,060 B1 * | | 6/2004 | Greenspan et al. ........ 424/489 |
| 7,141,520 B2 * | | 11/2006 | Zimmer et al. .............. 501/5 |
| 7,166,549 B2 * | | 1/2007 | Fechner et al. ............ 501/56 |
| 7,192,602 B2 * | | 3/2007 | Fechner et al. .......... 424/405 |
| 2002/0114768 A1 | | 8/2002 | Stoor et al. |

FOREIGN PATENT DOCUMENTS

| | | |
|---|---|---|
| WO | 96/10985 A1 | 4/1996 |
| WO | WO 97/27148 | 7/1997 |
| WO | 99/13852 A1 | 3/1999 |
| WO | WO 99/37287 | 7/1999 |
| WO | WO 00/15167 | 3/2000 |
| WO | WO 00/42977 | 7/2000 |
| WO | WO 00/76486 | 12/2000 |
| WO | WO 01/03650 | 1/2001 |
| WO | 01/72262 A2 | 4/2001 |
| WO | WO 01/72145 | 10/2001 |

OTHER PUBLICATIONS

European Search Report for EP 01922745.3 dated Mar. 10, 2006.
Supplementary European Search Report for European Application No. 04 784 897.3, dated Jul. 10, 2009.

* cited by examiner

*Primary Examiner*—Kevin Weddington
(74) *Attorney, Agent, or Firm*—Kramer Levin Naftalis & Frankel LLP

(57) ABSTRACT

Abrasive compositions which include bioactive materials, such as bioactive glass and bioactive ceramics, which provide biological properties such as anti-inflammatory, anti-microbial, anti-oxidant effects, improved wound healing, and/or other beneficial effects are provided. Also provided are abrasive compositions comprising relatively non-toxic, bioinert glasses and ceramics which provide good abrasive effects, reduce or eliminate potentially harmful small particles; reduce or eliminate clogging of dermabrasion equipment; possess a relatively large surface area for applying coatings; and may be inexpensive and simple to make. Methods for abrading human or animal tissue, such as human skin, by contacting such tissue with these abrasive compositions is also provided.

11 Claims, No Drawings

TISSUE ABRASIVES

CROSS REFERENCE APPLICATION

This application is a continuation in part of U.S. application Ser. No. 10/673,596 filed on Sep. 29, 2003 now abandoned, which is a continuation in part of U.S. application Ser. No. 09/818,466, filed on Mar. 27, 2001 now U.S. Pat. No. 7,250,174. The contents of each of these applications are incorporated herein in their entirety.

FIELD OF THE INVENTION

The present invention relates generally to biological tissue abrasives and, more specifically, to the use of bioactive materials, such as bioactive glass, bioactive ceramics, bioinert glass, and bioinert ceramics, for abrading tissue such as skin.

BACKGROUND OF THE INVENTION

A number of abrasive materials and methods are used to abrade, scrape, cleanse, massage, or buff the skin, scalp, fingernails, toenails, teeth, tongue or other body surfaces or body cavities of animals, and in particular, mammals such as humans.

Dermabrasion equipment is typically used to mechanically remove outer layers of skin to provide a fresh skin surface. One type of dermabrasion equipment is similar to a wire brush attached to an electric drill. One example of the more popular types is an apparatus that applies a stream of abrasive particles to skin under selectable pressure while simultaneously vacuuming the particles and flakes of skin debris into a waste container. This later type of dermabrasion equipment can simply remove the stratum corneum or penetrate deeply enough to remove the upper layers of the dermis. The process of applying abrasives can be repeated several times to achieve the desired effects.

Dermabrasion (which we use here to include dermaplaning, skin refinishing, skin resurfacing and surgical scraping) is used as a cosmetic procedure to improve the overall appearance of the skin, to reduce wrinkles, improve the appearance of scars or skin discoloration, and to remove pre-cancerous keratoses. Dermabrasion procedures generally penetrate deeper than chemical peels. By abrading down to the dermis layer, these procedures promote the production of collagen.

The abrasives currently used in dermabrasion equipment are typically 100-120 grit materials that include aluminum oxide, sodium bicarbonate and salt. Other abrasives including glass or polymeric beads have been proposed for use with dermabrasion equipment, which could be coated or mixed with beneficial agents such as anti-bacterials or other abrasives. One example of this is seen in International Patent Application No. WO 00139675 entitled "Skin Abrasion System and Method."

Another technique used to remove outer layers of skin is to manually scrub the face, for example, with pastes, creams or lotions that contain abrasives. Manual exfoliation mechanically removes outer layers of skin to provide a fresh skin surface, and has also been used to debride wounds. The abrasives currently used in manual scrubs include aluminum oxide, apricot pits, salt, olive pits, walnut shells, polyethylene beads, pumice, sodium tetraborate decahydrate granules and sugar. The abrasives are typically mixed into a carrier that often includes agents like moisturizers, emulsifiers, chelating agents, nutrients, and preservatives. Some examples can be found in U.S. Pat. No. 6,290,976 entitled "Facial Skin Dermabrasion Cleansing and Conditioning Composition;" U.S. Pat. No. 6,207,694 entitled "Pharmaceutical Compositions and Methods for Managing Scalp Conditions;" U.S. Pat. No. 5,939,085 entitled "Skin Smoothing Compositions Containing Hydroxyacids and Methods for Using Same;" and U.S. Pat. No. 5,866,145 entitled "Body Polisher."

However, these abrasive materials and systems have limited effectiveness. For example, these types of abrasives do not possess significant biological properties such as anti-inflammatory, anti-microbial, anti-irritant and anti-oxidant effects and cannot significantly accelerate or improve wound healing. In addition, these types of abrasives are known to clog dermabrasion equipment.

Accordingly, improved abrasive materials for machine or manual abrasion of human or animal tissue or body surfaces, such as human skin, would be highly advantageous. In particular, it would be advantageous if such abrasive materials provided significant properties such as anti-inflammatory, anti-microbial, anti-irritant and anti-oxidant effects as well as the acceleration and improvement of wound healing. In addition it would be advantageous if these improved abrasive materials were capable of minimizing or eliminating clogging of dermabrasion equipment.

It also would be advantageous for dermabrasion purposes to have non-toxic, non-bioactive (i.e., "bioinert") glasses and ceramics where such glass or ceramic provides good abrasive effects, reduces or eliminates potentially harmful small particles (i.e., "fines"), reduces or eliminates clogging of dermabrasion equipment, and possesses a relatively large surface area for applying coatings (e.g., anti-bacterial agents, lotions, vitamins and color). It also would be advantageous if such bioinert glasses and ceramics were relatively inexpensive and easy to manufacture.

SUMMARY OF THE INVENTION

Bioactive materials, such as bioactive glass and bioactive ceramics, are inorganic materials that possess certain biological properties. Applicants have surprisingly discovered that such bioactive materials may be utilized as abrasive materials for abrading animal tissue and body surfaces such as human skin, while providing effects superior to prior art abrasives and systems. When used as an abrasive material, the biological properties of these materials provide surprising benefits to the body surfaces being abraded. These bioactive abrasives can provide beneficial biological (or "bioactive") properties, including anti-inflammatory, anti-microbial, anti-irritant, remineralization and/or anti-oxidant effects, accelerated or improved wound healing, and/or other beneficial properties.

Accordingly the present invention provides abrasive materials for abrading animal tissue comprising a bioactive material, wherein the bioactive material is an inorganic material having such properties. Methods for preparing such materials are also provided.

The present invention also provides methods for abrading animal tissue, including human skin, comprising contacting the animal tissue with a bioactive material, wherein the bioactive material is an inorganic material having biological properties.

The present invention also provides abrasive materials for abrading animal tissue comprising non-toxic, non-bioactive (i.e., "bioinert") glasses and ceramics which possess one or more of the following advantageous properties: good abrasive effects, reduction or elimination of potentially harmful small particles (i.e., "fines"), reduction or elimination of the clogging of dermabrasion equipment, a relatively large surface area for applying coatings (e.g., anti-bacterial agents, lotions, vitamins), and relatively inexpensive and simple manufacturing processes. Methods for preparing such materials are also provided.

The present invention also provides methods for abrading animal tissue, including human skin, comprising contacting the animal tissue with abrasive materials comprising bioinert glass or ceramics. The present invention also provides abrasive materials for abrading animal tissue comprising bioactive glass or ceramics and bioinert glass or ceramics, in combination, and methods of making and using such abrasive materials.

DETAILED DESCRIPTION OF THE INVENTION

Bioactive materials, such as bioactive glass and bioactive ceramics, are non-toxic inorganic materials that can provide certain biological properties. Bioactive glasses and bioactive ceramics, according to particular embodiments of the present invention, are generally mineral oxides fused at high temperatures and milled into particles such that they release ions that react with a mammal's body. In exemplary embodiments these bioactive glasses and ceramics are materials that combine silicon, sodium, calcium and phosphorous oxides in various combinations.

As used herein, the term "bioactive" refers to substances having properties including anti-inflammatory, anti-microbial, anti-irritant and anti-oxidant effects as well as the acceleration and improvement of wound healing. In addition, "bioactive" refers to the mineral-building effects produced by the formation of hydroxyapatite on a surface.

As used herein, the term "bioactive glass" may refer to particulate melt-derived and/or sol-gel derived bioactive glass. In addition, the term "bioactive glass" may be used to refer to an aqueous extract of particulate melt-derived and/or sol-gel derived bioactive glass. Silicon-based bioactive glasses are amorphous, non-crystalline materials.

As used herein, the term "bioactive ceramic" includes bioactive inorganic non-metallic materials such as bioactive glass ceramics (materials which generally consist of a glassy and a crystalline phase), bioactive ceramics (materials which generally consist of a crystalline phase) and bioactive composite materials consisting of glasses, ceramics or other inorganic non-metallic substances.

As used herein, the term "ceramic" or "ceramics" also may refer to "glass ceramics" and related substances.

As used herein, the term "bioinert" refers to substances that are substantially not "bioactive" as the term "bioactive" is defined above, and substantially non-toxic to animals, such as humans, when used as an abrasive.

Certain embodiments of the present invention utilize bioactive glass which may comprise between about 30% and about 96% by weight of silicon dioxide oxide ($SiO_2$), between about 0% and about 35% by weight of sodium oxide ($Na_2O$), between about 4% and about 46% by weight calcium oxide (CaO), and between about 1% and about 15% by weight phosphorus oxide ($P_2O_5$). Such bioactive glass compositions may also comprise between about 0% and about 10% by weight of aluminum oxide ($Al_2O_3$). More preferably, the glass includes between about 30% and about 60% by weight of silicon dioxide oxide ($SiO_2$), between about 5% and about 30% by weight of sodium oxide ($Na_2O$), between about 10% and about 35% by weight calcium oxide (CaO), and between about 1% and about 12% by weight phosphorus oxide ($P_2O_5$).

Other embodiments of the present invention utilize bioactive phosphate glass which may comprise between about 0% and about 30 % by weight sodium oxide (Na2O), between about 0% and 30 % by weight potassium oxide ($K_2O$), between about 4% and about 46% by weight calcium oxide (CaO), and between about 10% and about 70% by weight phosphorus oxide ($P_2O_5$). Such bioactive phosphate glass compositions may also comprise between about 0% and about 25% by weight zinc oxide (ZnO) and between about 0% and 10% by weight aluminum oxide ($Al_2O_3$).

Bioactive glass ceramics may also be used as abrasive materials, and in methods of making and using such materials, in accordance with the present invention. Such bioactive glass ceramics may comprise between about 30% and about 96% by weight of silicon dioxide oxide ($SiO_2$), between about 0% and about 35% by weight of sodium oxide (Na2O), between about 4% and about 46% by weight calcium oxide (CaO), and between about 1% and about 15% by weight phosphorus oxide ($P_2O_5$). Preferably, the glass ceramics include between about 30% and about 60% by weight of silicon dioxide oxide ($SiO_2$), between about 5% and about 0% by weight of sodium oxide ($Na_2O$), between about 10% and about 35% by weight calcium oxide (CaO), and between about 1% and about 12% by weight phosphorus oxide ($P_2O_5$). The crystalline phases of bioactive glass ceramics may be various combinations of silicon, sodium and calcium within the ranges stated above. Compared to bioactive glasses, bioactive glass ceramics generally have a higher mechanical strength and greater Young's modulus value providing enhanced abrasive effects for these materials.

In certain embodiments of the present invention, other bioactive ceramics comprise calcium and phosphorus as the main components. Specific examples of these components include hydroxyapatite, tricalciumphospates and other calcium phosphates.

All of the bioactive and bioinert materials described herein may additionally include other anti-microbial or coloring agents or ions such as Ag, Co, Zn, Au, I, V, Cu, Fe, Nd, F and/or Ni, up to concentrations of about 5% by weight.

Applicants have surprisingly discovered that such bioactive materials may be utilized as abrasive material for human and animal tissues, and in particular human skin, while providing effects superior to prior art abrasives and systems. Such bioactive materials provide unexpectedly superior abrasive properties and are useful for both manual and mechanical abrasion. When used as an abrasive material, such bioactive materials can provide biological properties that benefit the body surfaces being abraded. Such biological properties can include, but are not limited to, anti-inflammatory, anti-microbial, anti-irritant, remineralization and/or anti-oxidant effects, acceleration or improvement of wound healing, and/or other beneficial properties.

Other constituents of the glasses or ceramics may include boron and magnesium. The preferred range for $B_2O_3$ is between about 0% and about 20% by weight, while the preferred range for MgO is between about 0% and about 10% by weight.

Abrasive compositions according to the present invention may also include various combinations or mixtures of bioactive materials with other glass or ceramic types such as borosilicate glasses, soda lime glasses, aluminum silicate glasses and phosphate glasses and other bioinert glasses. Other embodiments of the present invention provide compositions which may include natural or synthetic ceramics such as, for example, aluminum oxide, magnesium oxide, calcium carbonate, talc, mica, clay, pumice, porous glasses, aluminum nitride, boronitride, aluminum silicates, magnesium aluminum silicates or combinations of the above. Further embodiments of the present invention include glass ceramics such as lithium aluminum silicates, magnesium aluminum silicates and sodium calcium silicates or combinations of the above. Abrasive compositions also include various combinations of bioactive glasses, bioactive ceramics, bioinert glasses and bioinert glass ceramics. Borate glasses may be included in these compositions as well.

Bioactive materials such as bioactive glass and ceramics provide beneficial biological activity not provided by conventional abrasive materials. For example, aluminum oxide, a commonly used dermabrasive, can be described as a bioinert mineral oxide which does not provide significant beneficial biologic activities described above. Likewise, bioinert glass particles or polymeric beads do not provide beneficial biologic properties unless secondary materials are added. One example of this is seen in U.S. patent application No. 20010023351 entitled "Skin Abrasion System and Method".

Compositions and methods of making bioactive glasses and ceramics are well know by those skilled in the art, and are disclosed in numerous publications, including, for example, An Introduction to BioCeramics, L. Hench and J. Wilson eds. World Scientific, New Jersey (1993).

The present invention is related in part to the discovery that bioactive materials have a number of unexpected advantages over conventional abrasives. For example, besides the biological properties described above (e.g., anti-inflammatory, anti-microbial, anti-irritant anti-oxidant and/or wound healing effects), these materials may have optimal performance properties over the abrasives currently being used with manual scrub products or dermabrasion systems. For example, bioactive glass and ceramics are at least as effective in removing the surface of the skin as the best abrasives currently in use, such as aluminum oxide, and has far superior abrasion characteristics compared to some other abrasive materials such as sodium bicarbonate. In addition, for use in dermabrasion equipment, bioactive materials have superior flow characteristics providing excellent resistance to clogging such equipment. In sharp contrast, standard commercially available abrasives, such as aluminum oxide and sodium bicarbonate, often clog dermabrasion machines. Without being limited to any particular theory, it is believed that the improved performance of certain bioactive materials is due at least in part to the geometry and surface characteristics of these bioactive materials as well as reduced moisture sensitivity and reduced static charge build up of particles and equipment during use. Bioactive materials such as bioactive glass and bioactive ceramics may be used in a wide variety of dermabrasion systems such as those described in U.S. Pat. No. 6,511,486.

The ability to achieve precise particle sizes with bioactive materials is also advantageous. Bioactive materials can be manufactured in a broad range of grit or particle sizes. The manufacturing processes utilized to manufacture bioactive glass and ceramics, for example, can provide relatively precise control over the resulting particle sizes, and indeed, the uniformity of such particles. By different production technologies it is also possible to produce bioactive glass and bioactive ceramics in various shapes such as grinded particles, spheres, flakes, and fibers. Thus, powders having particles with a variety of aspect ratios may be obtained. These processes also may be applied to bioinert glasses and bioinert ceramics to control particle size and uniformity as well as the shape of the particles.

According to one aspect of the invention the preferred sizes for abrasive materials and for use in dermabrasion equipment are about 102 microns or about 122 microns, corresponding to the standard particle sizes used in dermabrasion equipment. However, larger or smaller particle sizes may be used in equipment capable of handling other particle sizes. Particle sizes for use in manual abrasives (e.g., facial scrubs) are generally above 200 microns, are preferably above 400 microns, and are more preferably around 600 microns. Particle sizes up to between 1-4 mm are also suitable as manual abrasives, especially for non-facial areas. However, it should be understood that other particle sizes and mixtures of particle sizes and particle size distributions are also within the scope of this invention.

The present invention also provides abrasive compositions which include combinations of particle sizes to optimize both abrasive and bioactive effects. For example, relatively small bioactive glass or ceramic particles (e.g., less than about 10 microns or even less than about 5 microns) can be combined with larger particle sizes (e.g., above about 50 microns or even more than about 100 microns). The relatively small particles can provide excellent bioactive effects while the relatively large particles provide excellent abrasive effects. If desired, smaller particles may be bonded to the surface of larger particles to minimize or eliminate potential "dusting" effects of the smaller particles. Such bonding may be accomplished, for example, by sintering or the use of bonding agents.

Further advantages of bioactive materials include the relatively insoluble nature of these materials as compared to many existing abrasives such as sodium bicarbonate and salt. Exemplary embodiments of bioactive glass and ceramics are stable in an aqueous environment.

The present invention also provides compositions which are mixtures of bioinert materials (e.g., borosilicate glass, alumina ceramics) and bioactive glasses or ceramics described herein. Such mixtures allow variations in the mechanical, chemical and biological properties of these bioactive materials such as hardness, water resistance, chemical stability and overall bioactivity which provides beneficial combinations between bioactivity and abrasive effects. At the same time such mixtures have reduced overall hygroscopy which minimizes potential clogging of abrasion equipment. Such mixtures can be made by combining the individual components together.

Melt-derived bioactive glass and bioactive ceramics may be produced by standard or specialty melting and milling processes. Such processes include, for example, melting in ceramic or platinum crucibles or tanks heated by gas or electrical heating mechanisms, dry milling (e.g., roller milling and air jet milling) and wet milling (e.g., attrition mills). Sol-gel processes alone or in combination with these other milling processes may also be used to produce these compositions. Such milling processes can produce particle size distributions in a variety of ranges (e.g., d50 values less than 500 microns, less than 200 microns, less than 100 microns, less than 50 microns, less than 10 microns, or even less than 2 microns).

The present invention also includes composite materials such as ceramic glass composites with bioactive or bioinert nanoparticles such as $TiO_2$, ZnO, CeO and/or hydroxyapatite are combined with bioactive or bioinert ceramic or glass particles. Preferably, to minimize agglomeration and potential inhalation, such nanoparticle compositions should be in a bonded form to minimize or eliminate these potential problems. Nanoparticles can provide a structured surface which provides particularly good abrasive effects. The nanoparticles may be fused onto the glass or ceramic particle surface using a sintering process or, alternatively, a sol-gel coating process may be used. Such compositions can also provide mineral building effects with the use of, for example, hydroxyapatite.

Other embodiments of the present invention provide coated bioactive particles and bioactive coatings on bioinert particles. This may be achieved, for example, by sol gel processes based on organic or inorganic raw materials. This provides enhanced anti-inflammatory, antimicrobial, antioxidant effects, and mineral building effects, for example. Other types of surface modifications of the powders, such as silanization provide enhanced hygroscopic and non-clogging properties. Thus, such compositions provide good flow properties and can minimize or eliminate clogging of dermabrasion equipment. Other coatings may include sol-gel derived glass as a coating for non-sol-gel derived glass or ceramics. Such sol-gel coating compositions display these same beneficial effects. Powders may be coated, for example, by spraying the sol-gel solution on the particles or by mixing the particles directly in a sol-gel solution. Subsequent heating converts the sol-gel into glass and fixes it onto the bioinert particle surface.

Abrasive compositions according to the present invention also may include other so-called "active" organic or inorganic materials such as fragrances, anti-irritants, antimicrobial and anti-inflammatory substances and/or other physiologically acceptable substances such as carriers, excipients, diluents, preservatives, buffers and/or solvents. These compositions also may be included in pharmaceutical preparations, especially those relating to dermatological care. In addition, color may be imparted to these compositions by using, for example, intrinsically colored powders or by coloring the powders with medical grade organic or inorganic agents.

Applicants have also unexpectedly discovered that other bioactive materials can provide biological properties such as those described above and thus, are useful as abrasives. Such bioactive materials include but are not limited to: zinc releasing compounds such as zinc containing bioactive glasses and ceramics, zinc oxide powder, and zinc stearate; silica containing bioactive glass or ceramics; silver releasing bioactive glass or ceramics; copper releasing bioactive glass or ceramics; magnesium releasing bioactive glass or ceramics; hydroxyapatite; and mineral salts or oxides such as copper, zinc, silver, magnesium and other bioactive metal complexes, and ceramic glass composites.

In addition to embodiments involving skin abrasion, the abrasives and methods disclosed herein are also appropriate for abrading other surfaces including but not limited to skin, scalp, fingernails, toenails, teeth, tongue and other body surfaces or body cavities of animals, and in particular, mammals such as humans. All of the above-described materials may be used as well in medical irrigation devices and procedures including wound care and cleansing of body cavities, surfaces and openings. These bioactive and bioinert materials may be included in a variety of solutions including, for example, emulsions, aqueous-based solutions, and collagen-containing solutions. In addition, these materials may be used in tissue cutting devices, solutions and procedures to provide combined abrasive and biological properties and effects. Further, these materials, also may be included in water pic type devices for oral or other use.

The present invention also provides abrasive materials comprising non-toxic, bioinert glasses and ceramics which possess one or more of the following advantageous properties: good abrasive effects, reduction or elimination of potentially harmful small particles (i.e., "fines"), reduction or elimination of the clogging of dermabrasion equipment, a relatively large surface area for applying coatings (e.g., antibacterial agents, lotions, vitamins); and relatively inexpensive and simple manufacturing processes.

In preferred embodiments such bioinert glasses and ceramics are substantially non-round. In other preferred embodiments such bioinert glasses and ceramics have edges. In still other preferred embodiments such bioinert glasses and ceramics are both substantially non-round and have edges. In other embodiments, bioinert glasses and ceramics have irregular shapes and/or a plurality of facets. Such bioactive glasses and ceramics possess superior abrasive and other properties compared to rounded particles such as glass beads and as compared to irregularly shaped aluminum oxide abrasives.

These bioinert glasses and ceramics may include, but are not limited to, borosilicate glasses, alkaline earth glasses and alumino silicate glasses. In an exemplary embodiment borosilicate glass may include between about 50% and about 85% silicon dioxide ($SiO_2$), between about 0% and about 25% by weight boron oxide ($B_2O_3$), between about 0% and about 20% by weight aluminum oxide ($Al_2O_3$), between about 0% and about 15% by weight sodium oxide ($Na_2O$), between about 0% and about 15% by weight potassium oxide ($K_2O$). Exemplary embodiments may also include calcium oxide (CaO), magnesium oxide (MgO), barium oxide (BaO), titanium oxide (TiO), strontium oxide (SrO), zerconium oxide ($ZrO_2$), lithium oxide ($Li_2O$), zinc oxide (ZnO), phosphorous oxide ($P_2O_5$), and fluorine (F) in amounts less than about 15% by weight individually or in combination. In addition, these bioinert glasses and ceramics may be doped with compounds or compositions which impart color to the glass or ceramic. The color-imparting substances may include elements such as Ag, Au, V, Cr, Co, Cu, Er, Nd, Fe, Mn, Ni, Sm, Eu, U and Se in amounts up to about 5% by weight individually or in combination. Other color imparting substances may be used as well.

In certain embodiments, rather than using multiple component bioinert glasses or ceramics, silica glass or ceramics may be used as the sole component. In certain embodiments, bioinert glasses may be ceramized.

Applicants have surprisingly discovered that these bioinert glasses and ceramics possess many advantages over conventional abrasive compositions such as aluminum oxide and rounded particles such as glass beads. Compared to aluminum oxide and rounded particles, bioinert glasses and ceramics according to the present invention possess at least one of the following benefits: good abrasive effects, reduction or elimination of potentially harmful small particles (i.e., "fines"), reduction or elimination of the clogging of dermabrasion equipment, a relatively large surface area for applying coatings (e.g., anti-bacterial agents, lotions, vitamins); and relatively inexpensive and simple manufacturing processes. In addition, bioinert glasses and ceramics according to the present invention may reduce potential acute health hazards associated with standard aluminum oxide based abrasives, such as eye, nose and throat irritation as well as potential chronic health hazards such as lung damage. Further, since compositions according to the present invention include aluminum oxide in amounts of about 20% or less, concerns about the potential links between aluminum and diseases such as Alzheimer's may be reduced.

The crystalline stability and melting properties of bioinert glasses and ceramics may permit melting of such glasses and ceramics in standard high volume refractory glass tanks in a continuous relatively low cost process. The raw materials used in these processes may also be acquired at a relatively low cost. In addition, these bioinert glasses and ceramics possess specific melt viscosities and low refractory corrosion. By rolling or simply casting into water, the melting process can produce "ribbons" or "frits." These ribbons or frits may be milled in, for example, roller mills, air mills or attrition mills to appropriate particle sizes and distributions.

These processes may be used to produce glass and ceramic particles with substantially non-round surfaces. Such non-round surfaces possess a significantly larger surface area to volume ratio as compared to rounded glass beads, for example. These non-round particles provide a much greater abrasive effect than substantially round particles.

The size distribution of these bioinert glasses and ceramics can be controlled and modified by the use of standard sieving processes or other techniques known in the art, such as wind sieving, for example. In addition, very small glass and ceramic particles may be sintered (via heat treatment) onto the surface of larger particles to reduce the amount of free small particles. The presence of fine particles may also be reduced by wind sieving or by the use of sedimentation methods.

If wet milling or mixing techniques are used, agglomeration of particles may be controlled by the drying process. Drying processes may include, for example, conventional drying in standard furnaces, spray drying, vacuum drying, freeze drying, supercritical drying, and microwave drying. These drying processes can also be used reduce the generation and presence of fine particles.

In one embodiment of the present invention, bioinert glasses and ceramics possess a high surface area to volume ratio which provides and excellent surface for coating these glasses and ceramics. These bioinert glasses and ceramics provide superior coating surfaces compared to conventional abrasives, such as aluminum oxide, and as compared to abrasives that are substantially round and smooth, such as glass beads. Coatings may include, but are not limited to, antimicrobial (e.g., antibacterial) agents, lotions, vitamins and/or color. Some embodiments of the present invention include bioinert glasses having porous, moderately porous or even highly porous surfaces, further increasing the relative surface area to volume ratio. Examples of porous bioinert glasses include sol gel produced silica (e.g., $SiO_2$), borosilicate glasses which may be produced by phase separation and leaching, and porous sinter glasses (e.g., soda lime glasses).

Coatings may be applied by mixing glass or ceramic powders with liquid silanes (silanization). Glass or ceramic powders may also be mixed with antimicrobial suspensions which may contain organic or inorganic antimicrobial compositions such as triclosan or salts of silver, zinc or copper. Various types of silanes may be added to the glass or ceramic powders in the mixing process to achieve the desired coating. In an exemplary embodiment the coating material may comprise up to about 15% by weight of the glass or ceramic particle. This amount can be adjusted to accommodate the specific surface area of the glass or ceramic particle and the desired thickness of the coating. Coatings may be applied before or after the drying process. Other coating techniques known in the art may also be used (e.g., spray coating).

In use these bioinert glasses and ceramics provide excellent abrasive effects. In addition, these bioinert glasses and ceramics display excellent flow properties making them particularly suitable for use in dermabrasion equipment where they will reduce or eliminate clogging of dermabrasion equipment.

For both the bioactive glasses and ceramics and the bioinert glasses and ceramics described above it is desirable to minimize the presence of heavy metals such as Pb, Cd, Hg, As and Sb. In one embodiment of the present invention such heavy metals are less than about 300 ppm. In a preferred embodiment these heavy metals are lower than about 100 ppm and in a more preferred embodiment less than about 50 ppm.

In addition, for both bioactive and bioinert glasses and ceramics it is useful for storage and commercial purposes to reduce the bioburden on these compositions. This can be achieved by using glasses or cermaics having bioactive properties or otherwise having antimicrobial properties (e.g., glasses comprising Ag, Zn, or Cu) or by providing bioinert glasses or ceramics with an antimicrobial coating. The bioburdens on these glasses and ceramics is preferably less that about 100 CFU and more preferably less than about 10 CFU.

The following examples illustrate various aspects of the present invention and should not be construed to limit the claims in any manner whatsoever.

EXAMPLES

Example 1

An abrasive having the following composition was formulated:

100% bioactive sodium calcium phosphosilicate glass (having approximately 45% $SiO_2$, 25% $Na_2O$, 25% CaO, and 5% $P_2O_5$) with a d50 value of 122 microns.

This abrasive composition has excellent bioactive and abrasive properties and displays excellent flow properties making it particularly suitable for use in dermabrasion equipment. In comparison, standard alumina based abrasion compositions have no bioactivity and frequently clog dermabrasion equipment.

Example 2

An abrasive having the following composition was formulated:

90% (by weight) borosilicate glass (having approximately 80.6% $SiO_2$, 12.5% $B_2O_3$, 2.4% $Al_2O_3$, 3.4% $Na_2O$, 0.5% $K_2O$ and small amounts of $TiO_2$, CaO, and MgO and standard refining agents, all by weight) with a d50 value of 122 microns.

10% (by weight) bioactive glass (having the same relative composition as used in Example 1) with a d50 value of 122 microns.

This abrasive composition has excellent bioactive and abrasive properties and displays excellent flow properties making it particularly suitable for use in dermabrasion equipment. In comparison, standard alumina based abrasion compositions have no bioactivity and frequently clog dermabrasion equipment.

Example 3

An abrasive having the following composition was formulated:

90% (by weight) borosilicate glass (having the same relative composition as used in Example 2) with a d50 value of 122 microns.

10% (by weight) bioactive glass (having the same relative composition as used in Example 1) with a d50 value of 10 microns.

This abrasive composition has excellent bioactive and abrasive properties and is particularly suited for use in or as a manual dermabrasion composition. In comparison, standard alumina based abrasion compositions have no bioactivity and frequently cause skin irritation.

Example 4

An abrasive having the following composition was formulated:

90% (by weight) borosilicate glass (having the same relative composition as used in Example 2) with a d50 value of 122 microns.

10% (by weight) bioactive glass (having the same relative composition as used in Example 1) with a d50 value of 122 microns.

This abrasive composition has excellent bioactive and abrasive properties and displays excellent flow properties making it particularly suitable for use in dermabrasion equipment. In comparison, standard alumina based abrasion compositions have no bioactivity and frequently clog dermabrasion equipment.

Example 5

An abrasive having the following composition was formulated:

90% (by weight) borosilicate glass (having the same relative composition as used in Example 2) with a d50 value of 102 microns.

5% (by weight) bioactive glass (having the same relative composition as used in Example 1) with a d50 value of 50 microns.

5% (by weight) nanoporous borosilicate glass ("Bioran") containing a fragrance with a d50 value of 50 microns.

This abrasive composition has excellent bioactive and abrasive properties.

Example 6

An abrasive having the following composition was formulated:

80% (by weight) alumina with a d50 value of 122 microns.

20% (by weight) bioactive glass (having the same relative composition as used in Example 1) and having a d50 value of 122 microns.

This abrasive composition has excellent bioactive and abrasive properties and is well suited for use with dermabrasion equipment.

Example 7

An abrasive having the following composition was formulated:

80% (by weight) natural magnesium aluminum silicate with a d50 value of 122 microns 20% (by weight) bioactive glass (with the same relative composition as used in Example 1) with a d50 value of 122 microns.

This abrasive composition has excellent bioactive and abrasive properties and displays excellent flow properties making it particularly suitable for use in dermabrasion equipment. In comparison, standard alumina based abrasion compositions have no bioactivity and frequently clog dermabrasion equipment.

Example 8

An abrasive having the following composition was formulated:

100% bioactive phosphate glass (having approximately 66.5% $P_2O_5$, 6.2% $Al_2O_3$, 12.5% $Na_2O$, 7.5% CaO, and 7.5% ZnO) with a d50 value of 122 microns.

This abrasive composition has excellent bioactive and abrasive properties and displays excellent flow properties making it particularly suitable for use in dermabrasion equipment. In comparison, standard alumina based abrasion compositions have no bioactivity and frequently clog dermabrasion equipment.

Example 9

An abrasive having the following composition was formulated:

100% bioactive glass ceramic (having the same relative composition as used in Example 1) with a d50 value of 122 microns where the crystalline phase is sodium calcium silicate with an overall amount greater than 30% by volume.

This abrasive composition has excellent bioactive and abrasive properties and displays excellent flow properties making it particularly suitable for use in dermabrasion equipment. In comparison, standard alumina based abrasion compositions have no bioactivity and frequently clog dermabrasion equipment.

Those skilled in the art will recognize that modifications and variations can be made without departing from the spirit of the invention. Therefore, it is intended that this invention encompass all such variations and modifications as fall within the scope of the appended claims.

Example 10

A borosilicate glass abrasive having the following composition by weight and a d50 value of 122 microns was formulated:
$SiO_2$-80.6%
$B_2O_3$-12.5%
$Al_2O_3$-2.4%
$Na_2O$-3.4%
$K_2O$-0.5% and small amounts of $TiO_2$, CaO, and MgO and standard refining agents. This abrasive composition has excellent abrasive properties and displays excellent flow properties making it particularly suitable for use in dermabrasion equipment.

Example 11

A boro alumino silicate glass abrasive having the following composition by weight and a d50 value of 122 microns was formulated:
$SiO_2$-75.0%
$B_2O_3$-10.5%
$Al_2O_3$-5.3%
$Na_2O$-7.0%
CaO-1.4%
BaO-0.54% and small amounts of $K_2O$, $TiO_2$ and MgO and standard refining agents. This abrasive composition has excellent abrasive properties and displays excellent flow properties making it particularly suitable for use in dermabrasion equipment.

Example 12

This borosilicate glass composition of Example 10 was mixed with 0.5% (by weight) of silane to produce a surface silanization which reduces or eliminates clogging.

Example 13

TABLE 1 below provides further examples of relatively low cost bioinert glasses having high chemical stability.
All constituents are listed by weight %.

|  | Glass 1 | Glass 2 | Glass 3 | Glass 4 | Glass 5 | Glass 6 | Glass 7 |
|---|---|---|---|---|---|---|---|
| $SiO_2$ | 75.0 | 70.0 | 80.5 | 68.9 | 57.0 | 72.3 | 54.9 |
| $B_2O_3$ | 10.4 | 11.2 | 12.7 | 1.0 | 8.0 | | 8.0 |
| $Al_2O_3$ | 5.3 | | 2.4 | 4.0 | 17.0 | 1.0 | 13.8 |
| $Na_2O$ | 7.0 | 9.5 | 3.5 | 12.6 | | 14.2 | 0.9 |
| $K_2O$ | 0.05 | 7.3 | 0.6 | 3.2 | | 0.2 | 0.2 |
| $LiO_2$ | | | | | | | |
| CaO | 1.4 | 0.2 | 0.02 | 5.05 | 2.0 | 8.0 | 20.8 |
| MgO | 0.02 | | 0.01 | 2.65 | 5.0 | 4.0 | 1.2 |
| BaO | 0.54 | 1.35 | 0.02 | 2.08 | 3.3 | 0.2 | |
| SrO | | | | | 6.0 | | |
| $TiO_2$ | 0.03 | 0.2 | 0.03 | | | | |
| $ZrO_2$ | | | 0.05 | | 1.0 | | |
| Minor components | to equal 100% | to equal 100% | to equal 100% | to equal 100% | to equal 100% | to equal 100% | to equal 100% |

Minor components can be e.g., standard refining agents.

Each of these abrasive compositions possess excellent abrasive properties and display excellent flow properties making them particularly suitable for use in dermabrasion equipment.

Example 14

Glass powder of Glass 6 in Example 13 having a d50 value of 100 microns was mixed with an aqueous solution of $AgNO_3$ (concentration of $AgNO_3$ in the aqueous solution 6% by wt.). The aqueous solution was mixed with the glass powder such that the aqueous solution comprises about 5% by weight of the mixture. This mixture was dried in a furnace at 550 C for 2 hours. The heating process allowed silver ions to penetrate the glass surface. The resulting glass powder has excellent antimicrobial properties.

What is claimed is:

1. A method for abrading human or animal skin comprising abrading the skin with a bioactive material which comprises between about 30% and about 96% by weight of silicon dioxide oxide ($SiO_2$), between about 0% and about 35% by weight of sodium oxide ($Na_2O$), between about 4% and about 46% by weight calcium oxide (CaO), and between about 1% and about 15% by weight phosphorus oxide ($P_2O_5$).

2. The method of claim 1, wherein the bioactive material comprises a zinc-releasing compound.

3. The method of claim 1, wherein the bioactive material comprises a silver-releasing compound.

4. The method of claim 1, wherein the bioactive material comprises a copper-releasing compound.

5. The method of claim 1, wherein the bioactive material comprises a magnesium-releasing compound.

6. The method of claim 1, wherein the bioactive material comprises mineral salts or oxides selected from the group consisting of copper, zinc, silver and magnesium.

7. The method of claim 1, wherein the bioactive material provides an anti-inflammatory effect.

8. The method of claim 1, wherein the bioactive material provides an anti-microbial effect.

9. The method of claim 1, wherein the bioactive material provides an anti-oxidant effect.

10. The method of claim 1, wherein the bioactive material accelerates or improves wound healing.

11. The method of claim 1, wherein the bioactive material comprises small particles bonded to larger particles.

* * * * *